(12) United States Patent
Li et al.

(10) Patent No.: US 11,980,440 B2
(45) Date of Patent: *May 14, 2024

(54) PHYSIOLOGICAL DETECTION DEVICE WITH DIFFERENT POLARIZERS

(71) Applicant: PixArt Imaging Inc., Hsin-Chu County (TW)

(72) Inventors: Ming-Chang Li, Hsin-Chu County (TW); Ren-Hau Gu, Hsin-Chu County (TW)

(73) Assignee: PIXART IMAGING INC., Hsin-Chu County (TW)

( * ) Notice: Subject to any disclaimer, the term of this patent is extended or adjusted under 35 U.S.C. 154(b) by 0 days.

This patent is subject to a terminal disclaimer.

(21) Appl. No.: 18/076,441

(22) Filed: Dec. 7, 2022

(65) Prior Publication Data
US 2023/0108436 A1 Apr. 6, 2023

Related U.S. Application Data

(63) Continuation of application No. 16/401,523, filed on May 2, 2019, now Pat. No. 11,583,183.

(51) Int. Cl.
*A61B 5/024* (2006.01)
*A61B 5/00* (2006.01)
*A61B 5/1455* (2006.01)

(52) U.S. Cl.
CPC ........ *A61B 5/0059* (2013.01); *A61B 5/02427* (2013.01); *A61B 5/02438* (2013.01); *A61B 5/14558* (2013.01); *A61B 5/7246* (2013.01); *A61B 2562/046* (2013.01)

(58) Field of Classification Search
CPC .............. A61B 5/0059; A61B 5/02427; A61B 5/02438; A61B 5/14558; A61B 5/7246; A61B 2562/046
See application file for complete search history.

(56) References Cited

U.S. PATENT DOCUMENTS

| | | | |
|---|---|---|---|
| 2011/0261300 A1* | 10/2011 | Miyazaki | G06F 3/042 356/614 |
| 2016/0242657 A1* | 8/2016 | Wang | A61B 5/0261 |
| 2017/0303801 A1* | 10/2017 | Lee | A61B 5/681 |
| 2019/0310487 A1* | 10/2019 | Mitani | G02B 27/281 |
| 2020/0379145 A1* | 12/2020 | Lin | B32B 7/03 |
| 2021/0190593 A1* | 6/2021 | Yao | G02B 5/3025 |
| 2022/0240862 A1* | 8/2022 | Lee | A61B 5/0059 |

FOREIGN PATENT DOCUMENTS

WO WO-2019066414 A1 * 4/2019 ........... G02B 5/0294

* cited by examiner

*Primary Examiner* — Rochelle D Turchen
(74) *Attorney, Agent, or Firm* — WPAT, P.C.

(57) ABSTRACT

There is provided a physiological detection device including a light source, a light detector, a processing unit and a display device. The light source emits light to illuminate a skin surface. The light detector receives the light from the skin surface to output detected signals. The processing unit confirms an attached state according to the detected signals and controls the display device to show an indication signal or a warning message when the attached state is confirmed not good.

10 Claims, 11 Drawing Sheets

PHYSIOLOGICAL DETECTION DEVICE WITH DIFFERENT POLARIZERS

RELATED APPLICATIONS

The present application is a continuation application of U.S. application Ser. No. 16/401,523, filed on May 2, 2019, the disclosure of which is hereby incorporated by reference herein in its entirety.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

BACKGROUND

1. Field of the Disclosure

This disclosure generally relates to a physiological detection device and, more particularly, to a physiological detection device capable of detecting an attached state thereof with a skin surface using an optical detection means.

2. Description of the Related Art

In recent years, it is intended to perform the physiological detection using the optical detection means since it has a smaller size and is noninvasive. Furthermore, this optical detection means can be integrated in a portable electronic device or a wearable electronic device such that the physiological detection can be easily performed in everyday life.

However, it is known that when an optical physiological detection device is arranged on a wearable device, the optical physiological detection device can have a relative movement with respect to an attached skin surface to cause noises in detected signals when the user is not at a static state. Especially, if the wearable device is not properly attached to and fixed on the skin surface, it is difficult to obtain correct detecting results. Complicated denoising algorithm must be used to remove the movement noises.

Accordingly, it is necessary to provide a physiological detection device that can confirm whether it is properly attached to a skin surface before the physiological detection is started to increase the detection accuracy.

SUMMARY

The present disclosure provides a physiological detection device that confirms a wearing state or an attached state with respect to a skin surface by comparing detected signals of different pixels located under different polarizers.

The present disclosure further provides a physiological detection device that confirms a wearing state or an attached state with respect to a skin surface by identifying brightness distribution of an image frame outputted by a sensor array.

The present disclosure further provides a physiological detection device that confirms a wearing state or an attached state with respect to a skin surface by calculating a time-of-flight detected by a single photon avalanche diode (SPAD).

The present disclosure provides a physiological detection device including a sensor array, a polarizing layer and a processing unit. The polarizing layer includes a first region and a second region having different polarization directions. The sensor array is opposite to the polarizing layer and configured to receive light from a skin to output pixel data. The processing unit is electrically connected to the sensor array to receive the pixel data, and configured to generate a first detected signal associated with the first region, generate a second detected signal associated with the second region, and compare the first detected signal with the second detected signal to determine an attached state of the physiological detection device with respect to the skin.

The present disclosure further provides a physiological detection device including a sensor array, a polarizing layer and a processing unit. The polarizing layer includes a first region having a first polarization direction and a second region having a second polarization direction, different from the first polarization direction. The sensor array is opposite to the polarizing layer and configured to receive light from a skin to output pixel data. The processing unit is electrically connected to the sensor array to receive the pixel data, and configured to generate a first detected signal and a second detected signal associated with the first polarization direction respectively at a first time point and a second time point, generate a third detected signal and a fourth detected signal associated with the second polarization direction respectively at the first time point and the second time point, and compare a first difference between the first detected signal and the second detected signal with a second difference between the third detected signal and the fourth detected signal to determine an attached state of the physiological detection device with respect to the skin.

The present disclosure further provides a physiological detection device including a sensor array, a polarizing layer and a processing unit. The polarizing layer includes a first region having a first polarization direction and a second region having a second polarization direction, different from the first polarization direction. The sensor array is opposite to the polarizing layer and configured to successively receive light of a first wavelength and light of a second wavelength from a skin to output pixel data. The processing unit is processing unit, electrically connected to the sensor array to receive the pixel data, and configured to generate a first detected signal associated with the first polarization direction and the light of first wavelength, generate a third detected signal associated with the first polarization direction and the light of second wavelength, generate a second detected signal associated with the second polarization direction and the light of first wavelength, generate a fourth detected signal associated with the second polarization direction and the light of second wavelength, and compare the first detected signal with the third detected signal, and compare the second detected signal with the fourth detected signal to determine an attached state of the physiological detection device with respect to the skin.

In the physiological detection device of the present disclosure, although the attached or wearing state detection is illustrated herein by using the optical detection means, it is not to limit the present disclosure. The physiological detection may be performed by optical ways or non-optical (e.g., using electrodes) ways without being limited to those illustrated in the present disclosure.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

It should be noted that, wherever possible, the same reference numbers will be used throughout the drawings to refer to the same or like parts.

The physiological detection device of every embodiment of the present disclosure is applicable to a portable electronic device (e.g., a smart phone) or a wearable electronic device (e.g., a smart watch or a smart bracelet). Before starting to detect the physiological characteristics such as the heart rate, blood oxygen saturation and/or microcirculation of skin, the physiological detection device firstly detects whether it is properly attached (e.g., tight enough) to a skin surface, and the physiological detection is then performed only after a wearing state or an attached state is confirmed to be good.

Figure 1A:
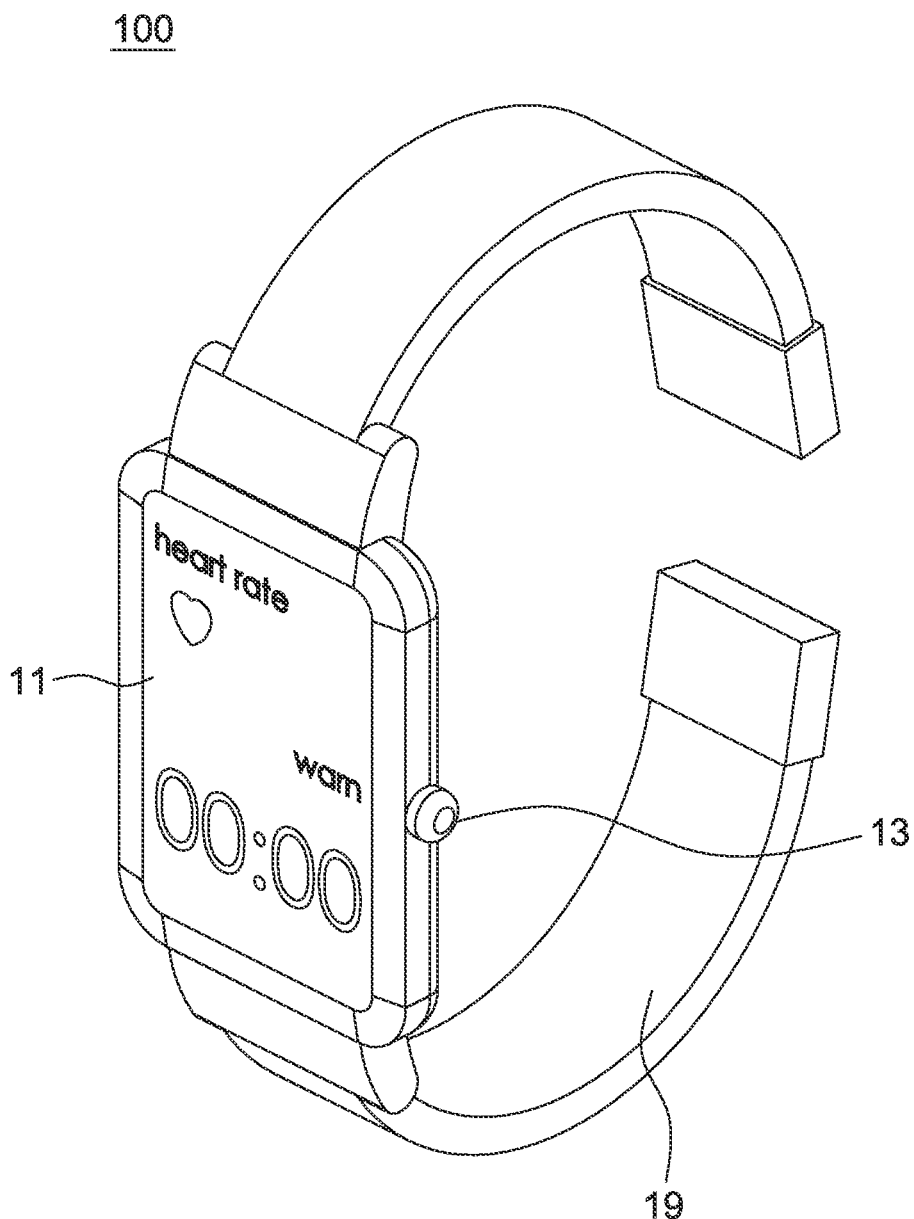
FIG. 1A is a front view of a wearable device according to one embodiment of the present disclosure.
Figure 1B:
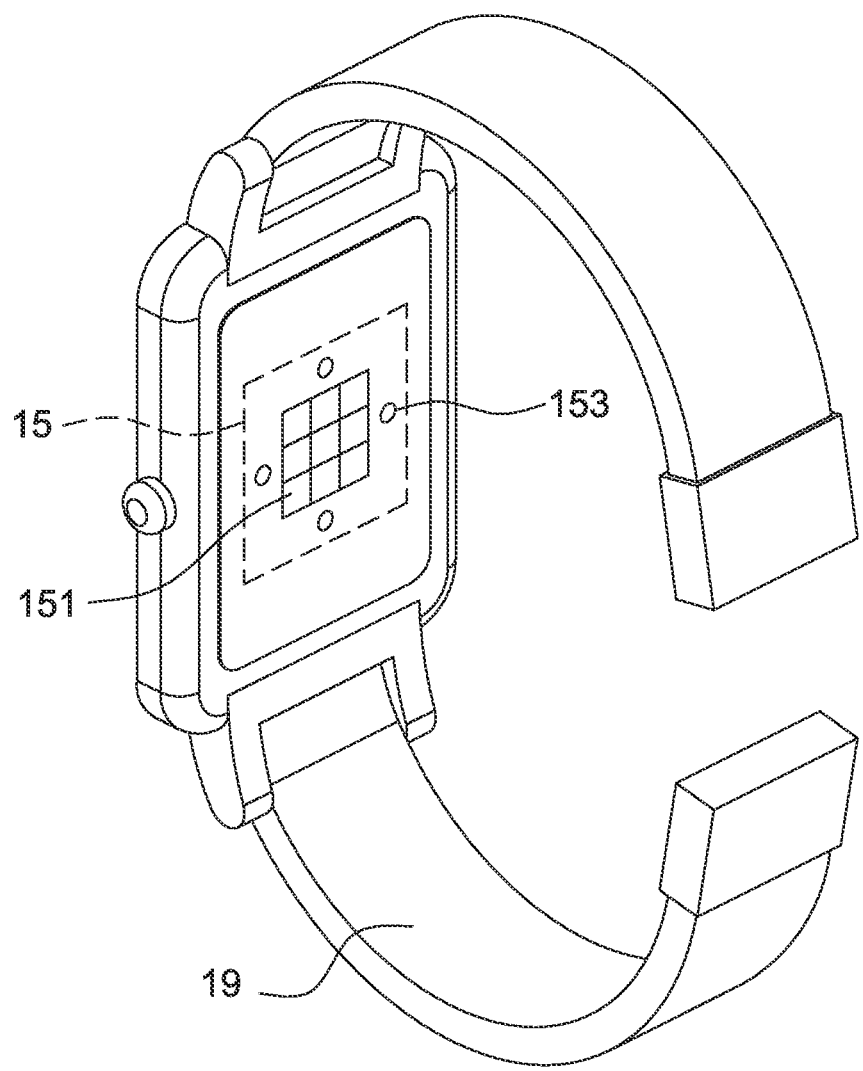
FIG. 1B is a bottom view of the wearable device of FIG. 1A showing a physiological detection device arranged thereon.

Referring to FIGS. 1A and 1B, FIG. 1A is a front view of a wearable device 100 according to one embodiment of the present disclosure; and FIG. 1B is a bottom view of the wearable device 100 in FIG. 1A. The physiological detection device 15 of the present disclosure is shown to be located on a bottom surface of the wearable device 100. It should be mentioned that although FIGS. 1A and 1B show that the wearable device 100 is a watch, it is only intended to illustrate but not to limit the present disclosure. The physiological detection device 15 of the present disclosure is arranged on any electronic device as long as the electronic device has a contact with the user's skin during operation.

The wearable device 100 includes a display device 11, a knob 13, a physiological detection device 15 and a belt 19. The belt 19 is used to fix the wearable device 100 on a user's forearm, and is formed by any suitable material and structure without particular limitations. In one non-limiting aspect, the knob 13 is used to alter the contents shown on the display device 11.

The display device 11 has a LCD screen, OLED screen or the like used to show detected physiological characteristics, time and an indication signal thereon. The indication signal informs a user regarding whether the wearable device 100 is properly worn for the physiological detection. It is appreciated that locations, patterns and sizes of the contents shown on the display device 11 are properly arranged without being limited to those shown in FIG. 1A.

The physiological detection device 15 is arranged on a proper surface, which is easily to be attached to a user's skin surface, of the wearable device 100. The physiological detection device 15 includes a sensor array 151 and at least one light source 153 (e.g., 4 light sources shown in FIG. 1B) arranged adjacent to a side of the sensor array 151.

It should be mentioned that when arranging on a portable electronic device, the physiological detection device 15 is arranged on any surface of the portable electronic device as long as the user can put his/her finger thereon.

The sensor array 151 is a photodiode array (e.g., CMOS sensor array), and each pixel (e.g., using 3 T, 4 T or 5 T pixel structure) has at least one photodiode for outputting intensity value as pixel data. Or, the sensor array 151 is a single photon avalanche diode (SPAD) array, and each pixel has one SPAD for outputting electrical pulse signals to be counted as pixel data. The operation of the CMOS sensor array and the SPAD is known to the art, and thus details thereof are not described herein.

Figure 1C:
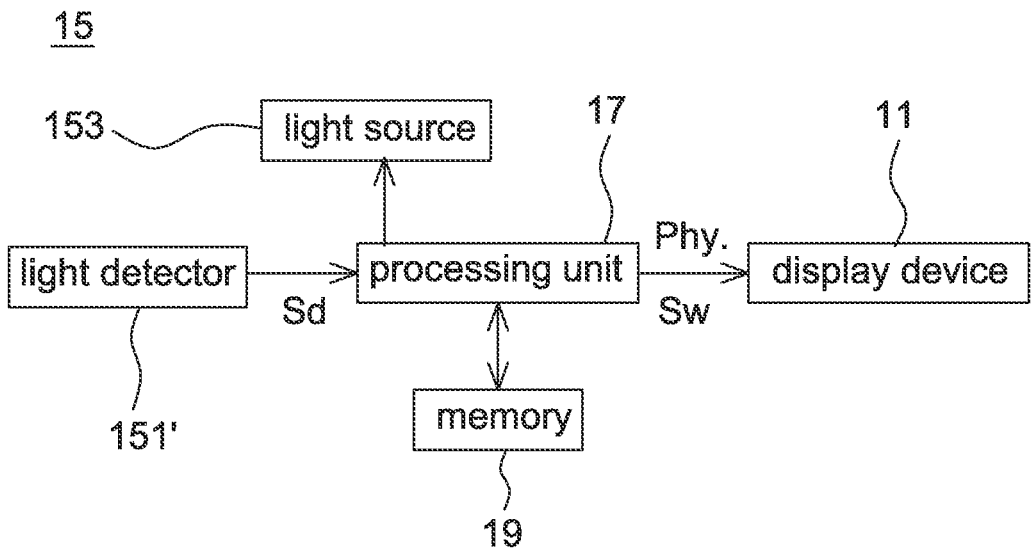
FIG. 1C is a block diagram of a physiological detection device according to one embodiment of the present disclosure.

Referring to FIG. 1C, it is a block diagram of a physiological detection device 15 according to one embodiment of the present disclosure. The physiological detection device 15 includes the light source 153, a light detector 151' and a processing unit 17. The physiological detection device 15 is connected to a display device 11, and coupled to a memory 19 which is accessed by the processing unit 17 during operation. The light detector 151' is a sensor array or a SPAD illustrated by examples below. The processing unit 17 is a digital signal processor (DSP) or an application specific integrated circuit (ASIC) which is electrically connected to the light source 153 and the light detector 151' to control the light source 153 to emit light corresponding to the light sensing of the light detector 151'. The memory 19 includes a volatile memory and/or a non-volatile memory used to store a predetermined threshold for being accessed by the processing unit 17 and compared with a detected result Sd from the light detector 151'. The processing unit 17 outputs calculated physiological characteristics Phy. and an indication signal Sw to the display device 11 to be shown thereon.

Figure 2:
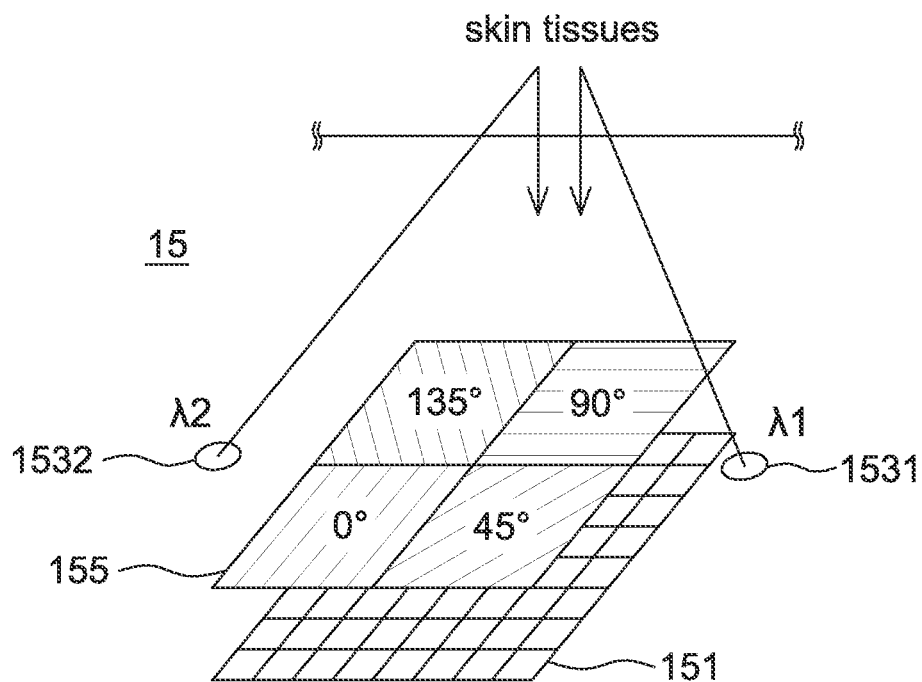
FIG. 2 is a schematic diagram of a physiological detection device according to a first embodiment of the present disclosure.

Referring to FIG. 2, it is a schematic diagram of a physiological detection device 15 according to a first embodiment of the present disclosure. The physiological detection device 15 includes a sensor array 151, a first light source 1531 and a polarizing layer 155.

The first light source 1531 emits light of a first wavelength $\lambda 1$ and having a first polarization direction (e.g., 0° herein) to illuminate a skin. For example, a polarizer is integrated with or arranged in front of an emission direction of the first light source 1531 to cause the emitted light to have the first polarization direction. The first light source 1531 is a light emitting diode or a laser diode. The first wavelength $\lambda 1$ is preferably selected from one wavelength between the green light spectrum and the infrared light spectrum.

The sensor array 151 has multiple pixels arranged in a matrix. The multiple pixels are divided into a first pixel region and a second pixel region respectively output first pixel data and second pixel data when the first light source 1531 is being turned on. The pixel data outputted by one pixel region herein is processed by the processing unit 17 separately from the pixel data from a different pixel region during identifying an attached state.

The polarizing layer 155 is covered or coated upon the sensor array 151. The polarizing layer 155 has a first region (e.g., 0° region) having the first polarization direction and opposite to the first pixel region. The polarizing layer 155 has a second region (e.g., 90° region) opposite to the second pixel region and having a second polarization direction perpendicular to the first polarization direction. In this way, pixels under the first region only receives light of the first polarization direction, and pixels under the second region only receives light of the second polarization direction.

The processing unit 17 (referring to FIG. 1C) is electrically connected to the first light source 1531 and the sensor array 151. The processing unit 17 generates a first detected signal according to the first pixel data, e.g., calculating an average brightness value of the first pixel data as the first detected signal, or summing the first pixel data at different times to obtain a first photoplethysmography (PPG) signal and using an amplitude of the first PPG signal as the first detected signal. Similarly, the processing unit 17 generates a second detected signal according to the second pixel data, e.g., calculating an average brightness value of the second pixel data as the second detected signal, or summing the second pixel data at different times to obtain a second PPG signal and using an amplitude of the second PPG signal as the second detected signal.

The processing unit 17 then compares the first detected signal with the second detected signal to determine an attached state of the physiological detection device 15 with respect to the skin (or a wearing state of the wearable device 100). For example referring to FIGS. 3A and 3B, FIG. 3A shows an image frame $IF_{0\lambda 1}$ outputted by the sensor array 151 when the physiological detection device 15 is attached well with the skin; and FIG. 3B shows an image frame $IF_{1\lambda 1}$ outputted by the sensor array 151 when the physiological detection device 15 has a distance D from the skin.

Figure 3A:
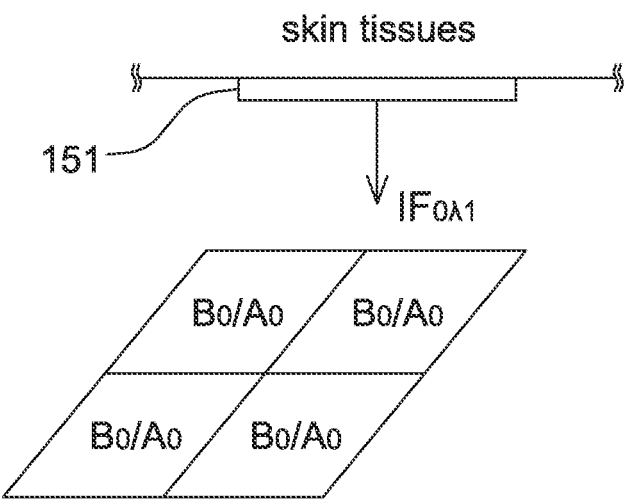
FIGS. 3A-3D are schematic diagrams of the brightness or amplitude distribution of an image frame outputted by a physiological detection device according to the first embodiment of the present disclosure.
Figure 3B:
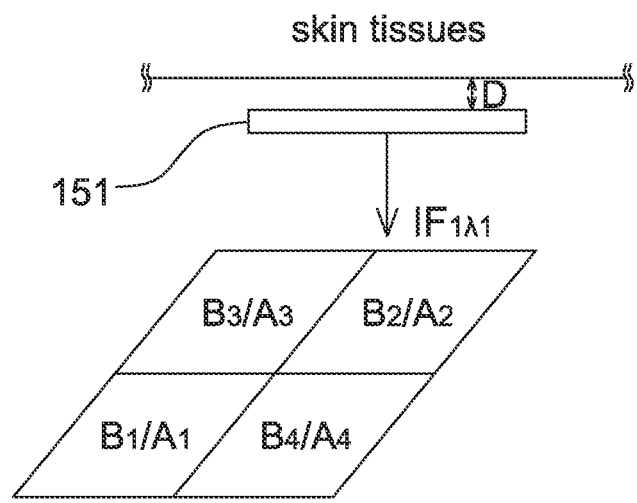

If the physiological detection device 15 is attached well, values of the first detected signal and the second detected signal are substantially identical, e.g., average brightness values of all pixel regions being $B_0$ and amplitudes of PPG signal of all pixel regions being $A_0$ in FIG. 3A. However, if the physiological detection device 15 is separated from the skin, values of the first detected signal and the second detected signal have a difference therebetween due to the polarization of reflected light being altered by skin tissues, e.g., the average brightness value of the first pixel region being $B_1$ and the amplitude of PPG signal of the first pixel region being $A_1$; the average brightness value of the second pixel region being $B_2$ and the amplitude of PPG signal of the second pixel region being $A_2$ in FIG. 3B, wherein $B_1 \neq B_2$ and $A_1 \neq A_2$.

Accordingly, the processing unit 17 is arranged to determine the attached state being good when a difference between the first detected signal and the second detected signal ($|B_1-B_2|$ or $|A_1-A_2|$) is lower than a difference threshold; and determine the attached state being bad when the difference between the first detected signal and the second detected signal is larger than the difference threshold. The difference threshold is previously determined and stored in the memory 19.

This embodiment further compares a variation of the first detected signal and a variation of the second detected signal to determine whether the physiological detection device 15 is attached well. For example, at a first time point at which the physiological detection device 15 is attached to the skin as FIG. 3A, an average brightness values $B_{01}$ (or an amplitude $A_{01}$) from the 0-degree region is obtained and an average brightness values $B_{02}$ (or an amplitude $A_{02}$) from the 90-degrees region is obtained; at a second time point at which the physiological detection device 15 is distanced from the skin by D as FIG. 3B, an average brightness values B (or an amplitude $A_1$) from the 0-degree region is obtained and an average brightness values $B_2$ (or an amplitude $A_2$) from the 90-degrees region is obtained.

The processing unit 17 is arranged to determine the attached state being good when a variation difference $||B_1-B_{10}|-|B_2-B_{20}||$ (or $||A_1-A_{10}|-|A_2-A_{20}||$) between a variation of the first detected signal $|B_1-B_{10}|$ (or $|A_1-A_{10}|$) and a variation of the second detected signal $|B_2-B_{20}|$ (or $|A_2-A_{20}|$) is lower than a difference threshold; and determine the attached state being bad when the variation difference between the variation of the first detected signal and the variation of the second detected signal is larger than the difference threshold, where $B_{10}$ is identical to or different from $B_{20}$; and $A_{10}$ is identical to or different from $A_{20}$.

In order to inform the user when the physiological detection device 15 is not attached well, the processing unit 17 is further arranged to control the display device 11 (referring to FIGS. 1A and 1C) to show an indication signal (e.g., by a proper message including a graph, characters and/or numbers) when the attached state is determined to be bad. In some aspects, the user is formed by other signals such as light of a lamp, vibration caused by a vibrator, or sound outputted by a speaker without particular limitations as long as the user is informed.

In some aspects, the sensor array 151 is further divided into a third pixel region and a fourth pixel region. The polarizing layer 155 further includes a third region (e.g., 45° region in FIG. 2) opposite to the third pixel region and having a third polarization direction with 45 degrees difference from the first polarization direction, and a fourth region (e.g., 135° region in FIG. 2) opposite to the fourth pixel region and having a fourth polarization direction with 135 degrees difference from the first polarization direction.

Similarly, if the physiological detection device 15 is attached well, values of the detected signals (e.g., $B_0$ and $A_0$) outputted from different pixel regions corresponding to different polarizer regions are substantially identical. But if the physiological detection device 15 is separated from the skin, a variation between values of the detected signals (e.g., $B_1$ to $B_4$ or $A_1$ to $A_4$) outputted from different pixel regions corresponding to different polarizer regions is induced. The processing unit 17 compares different detected signals to confirm the attached state, e.g., calculating a variance between the detected signals (e.g., $B_1$ to $B_4$ or $A_1$ to $A_4$), e.g., good attachment being confirmed if the variance is smaller than a variance threshold, and bad attachment being confirmed if the variance is larger than the variance threshold.

To improve the identification accuracy, the physiological detection device 15 further includes a second light source 1532 used to emit light of the first polarization direction and having a second wavelength λ2 different from the first wavelength λ1 to illuminate the skin. The second light source 1532 is arranged at the same side of the sensor array 151 with the first light source 1531 or at a different side (e.g., an opposite side shown in FIG. 2). Preferably, a wavelength difference between the first wavelength λ1 and the second wavelength λ2 is at least 50 nm to make the variation between different light sources be apparent enough. The processing unit 17 further generates a third detected signal according to third pixel data generated by the first pixel region when the second light source 1532 is turned on; and generates a fourth detected signal according to fourth pixel data generated by the second pixel region when the second light source 1532 is turned on.

Figure 3C:
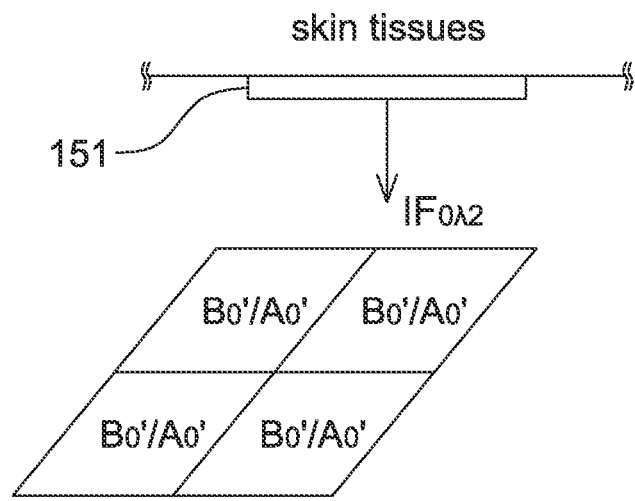
Figure 3D:
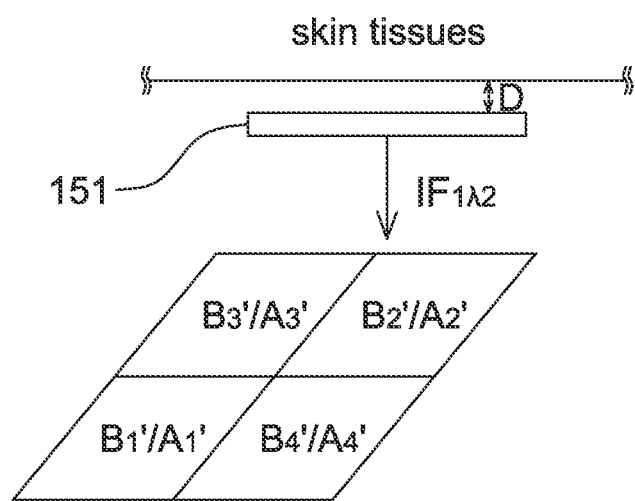

FIGS. 3C and 3D respectively show image frames $IF_{0\lambda2}$ and $IF_{1\lambda2}$ corresponding to the lighting of the second light source 1532, wherein FIG. 3C shows good attachment and FIG. 3D shows bad attachment. In addition to comparing the detected signals within the same image frame (e.g., $B_1'$ to $B_4'$ or $A_1'$ to $A_4'$), the processing unit 17 further compares the detected signals between different image frames $IF_{0\lambda2}$ and $IF_{1\lambda2}$, e.g., comparing the first detected signal (e.g., $B_1$ or $A_1$) and second detected signal (e.g., $B_2$ or $A_2$) obtained when the first light source 1531 is turned on respectively with the third detected signal (e.g., $B_1'$ or $A_1'$) and the fourth detected signal (e.g., $B_2'$ or $A_2'$) obtained when the second light source 1532 is turned on to determine the attached state.

More specifically, if the physiological detection device 15 is attached well with the skin, $B_1$ and $B_1'$ (or $A_1$ and $A_1'$) have a first relationship as well as $B_2$ and $B_2'$ (or $A_2$ and $A_2'$) have a second relationship. If the physiological detection device 15 leaves the skin more than a predetermined distance, the deviation between $B_1$ and $B_1'$ (or $A_1$ and $A_1'$) and/or $B_2$ and $B_2'$ (or $A_2$ and $A_2'$) becomes large enough such that the processing unit 17 confirms the bad attachment condition by calculating the deviation.

This embodiment further compares a variation of the third detected signal and a variation of the fourth detected signal to determine whether the physiological detection device 15 is attached well. For example, at a first time point at which the physiological detection device 15 is attached to the skin as FIG. 3C, an average brightness values $B_{01}'$ (or an amplitude $A_{01}'$) from the 0-degree region is obtained and an average brightness values $B_{02}'$ (or an amplitude $A_{02}'$) from the 90-degrees region is obtained; at a second time point at which the physiological detection device 15 is distanced from the skin by D as FIG. 3D, an average brightness values $B_1'$ (or an amplitude $A_1'$) from the 0-degree region is obtained and an average brightness values $B_2'$ (or an amplitude $A_2'$) from the 90-degrees region is obtained.

The processing unit 17 is arranged to determine the attached state being good when a variation difference $|B_1'-B_{10}'|-|B_2'-B_{20}'|$ (or $|A_1'-A_{10}'|-|A_2'-A_{20}'|$) between a variation of the third detected signal $|B_1'-B_{10}'|$ (or $|A_1'-A_{10}'|$) and a variation of the fourth detected signal $|B_2'-B_{20}'|$ (or $|A_2'-A_{20}'|$) is lower than a difference threshold; and determine the attached state being bad when the variation difference between the variation of the third detected signal and the variation of the fourth detected signal is larger than the difference threshold, where $B_{10}'$ is identical to or different from $B_{20}'$; and $A_{10}'$ is identical to or different from $A_{20}'$.

Similarly, the processing unit 17 identifies the attached state according to the relationship of more pixel regions, e.g., between $B_3$ and $B_3'$ (or $A_3$ and $A_3'$) and/or between $B_4$ and $B_4'$ (or $A_4$ and $A_4'$) shown in FIGS. 3A-3D.

More specifically, since the changing of the distance D has different effects on light of different wavelengths, using light of different wavelengths helps to define more distance steps. For example, at a first suspension distance, B3 (or A3) is substantially identical to B3' (or A3'); whereas, at a second suspension distance different from the first suspension distance, B3 (or A3) is deviated from B3 (or A3). Accordingly, different deviations |B3-B3'| (or |A3-A3'|) are used to define different distances D, respectively.

Furthermore, since the changing of the distance D has different effects on light (identical wavelength) passing through different polarizers, using polarizers having different polarization directions helps to define more distance steps. For example, at a first suspension distance, B3 (or A3) is substantially identical to B1 or B2 (A1 or A2); whereas, at a second suspension distance different from the first suspension distance, B3 (or A3) is deviated from B1 or B2 (A1 or A2). Accordingly, different deviations |B3-B1| or |B3-B2| (or |A3-A1| or |A3-A2|) are used to define different distances D, respectively.

Figure 4:
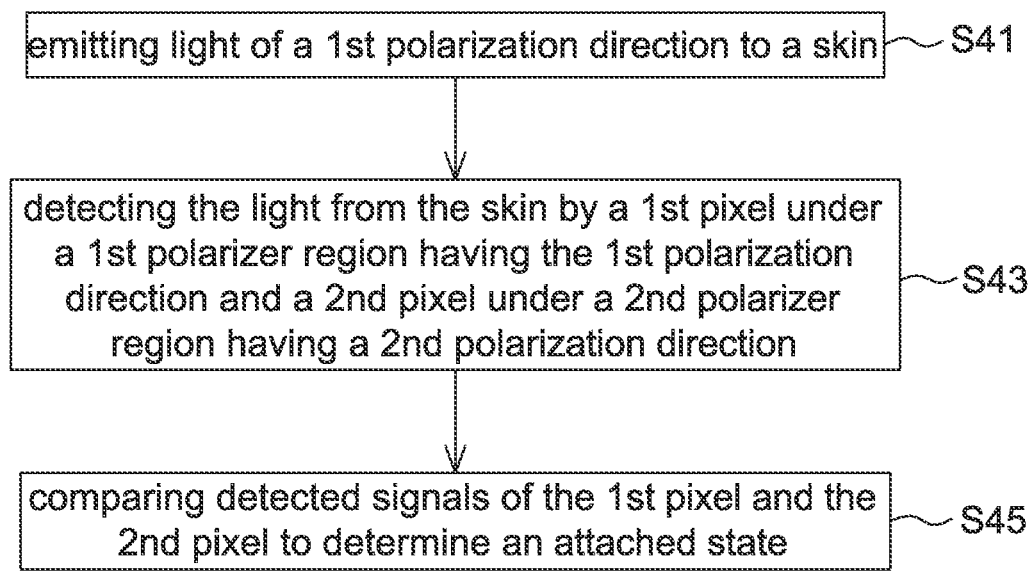
FIG. 4 is a flow chart of an operating method of a physiological detection device according to the first embodiment of the present disclosure.

Referring to FIG. 4, it is a flow chart of an operating method of a physiological detection device according to the first embodiment of the present disclosure. The operating method includes the steps of: emitting light of a first polarization direction to a skin (Step S41); detecting the light from the skin by a first pixel under a first polarizer region having the first polarization direction and a second pixel under a second polarizer region having a second polarization direction (Step S43); and comparing detected signals of the first pixel and the second pixel to determine an attached state (Step S45). Details of the operating method have been illustrated above, and thus details thereof are not repeated herein. If the polarizing layer 155 having more polarizer regions, the processing unit 17 compares a variance of the detected signals with a variance threshold.

It should be mentioned that although the first light source 1531 and the second light source 1532 are illustrated by emitting light of a first polarization direction, it is only intended to illustrate but not to limit the present disclosure. In other embodiments, the first light source 1531 and the second light source 1532 are arranged to emit light of other polarization directions, identical to or different from 45°, 90° or 135°. The processing unit 17 compares detected signals of difference pixels under different polarizer regions to determine an attached state according to the relationship between said detected signals as long as said relationship is previously stored in the memory 19.

Figure 5:
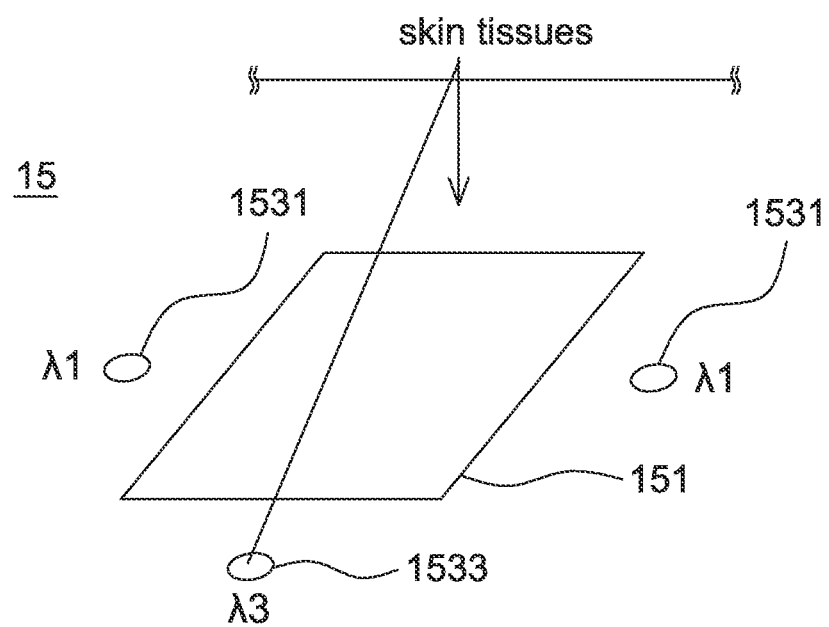
FIG. 5 is a schematic diagram of a physiological detection device according to a second embodiment of the present disclosure.

Referring to FIG. 5, it is a schematic diagram of a physiological detection device according to a second embodiment of the present disclosure. The physiological detection device 15 includes a light source 1533, a sensor array 151 and a processing unit 17 (referring to FIG. 1C).

The light source 1533 emits light to illuminate a skin, and the light preferably has a wavelength λ3 within a green light spectrum, e.g., green light LED or green light laser diode. The light source 1533 is arranged at a side of the sensor array 151.

The sensor array 151 includes multiple pixels to receive the light from the skin to output an image frame. As mention above, the sensor array 151 is a photodiode array or a SPAD array.

The processor unit 17 is electrically connected to the light source 1533 and the sensor array 151, and determines an attached state according to a brightness distribution of the image frame. More specifically, the processing unit 17 identifies every bright pixel in the image frame having a gray value higher than a brightness threshold, identify a bright region covering all bright pixels in the image frame, and determine the attached state according to a position of the bright region in the image frame. The brightness threshold is previously determined and stored in the memory 19.

Figure 6A:
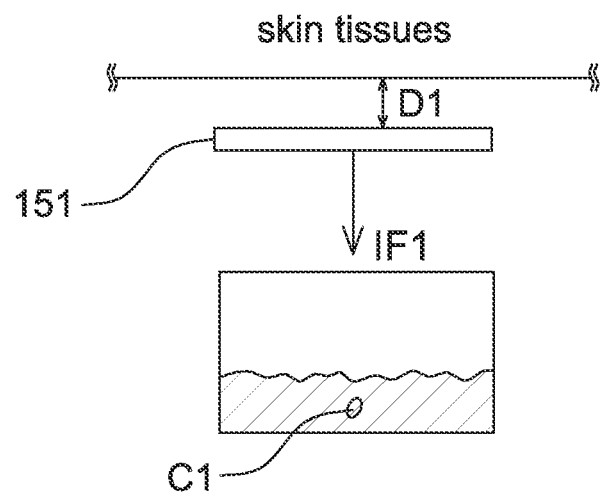
FIGS. 6A-6B are schematic diagrams of the brightness distribution of an image frame outputted by a physiological detection device according to the second embodiment of the present disclosure.
Figure 6B:
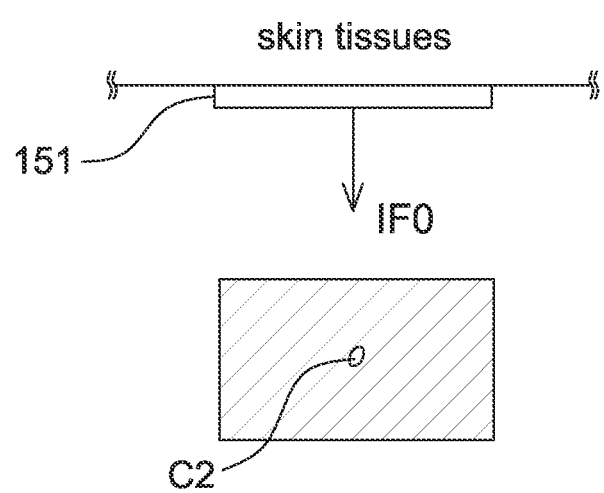

Referring to FIGS. 6A and 6B, FIG. 6A shows an image frame IF1 outputted by the image sensor 151 when the physiological detection device 15 is distanced from the skin by a distance D1; and FIG. 6B shows an image frame IF0 outputted by the image sensor 151 when the physiological detection device 15 is well attached to the skin. In FIG. 6A, when the physiological detection device 15 is not directly attached to the skin, a bright region (e.g., the region filled with inclined lines) appears in a pixel region at a side of the image sensor 151 adjacent to the light source 1533. In FIG. 6B, when the physiological detection device 15 is well attached to the skin, the bright region is substantially distributed with the whole pixels of the sensor array 151. Accordingly, in the present disclosure, it is able to determine the attached state according to the bright region, e.g., the distribution, location or size thereof.

For example, when the bright region is associated with pixels at a side of the sensor array 151 adjacent to the light source 1533, the attached state is determined to be bad; and when the bright region covers the whole sensor array 151, the attached state is determined to be good.

In another aspect, the processing unit 17 further calculates a center (e.g., gravity center or mass center) of the bright region in the image frame, and associates the calculated center of the bright region in the image frame with the sensor array 151. When the center (e.g., C1 in FIG. 6A) is associated with a pixel position closer to a side of the sensor array 151 (e.g., lower side in FIG. 6A) adjacent to light source 1533 than an opposite side (e.g., upper side in FIG. 6A) of the sensor array 151, the attached state is determined to be bad. On the other hand, when the center (e.g., C2 in FIG. 6B) is substantially at an array center of the sensor array 151, the attached state is determined to be good. A deviation threshold from the array center is previously determined and stored in the memory 19. When the deviation of the center is larger than the deviation threshold, the attachment is confirmed to be bad.

In another aspect, if a size of the bright region is smaller than a size threshold, the attached state is determined to be bad. On the other hand, if a size of the bright region is larger than the size threshold, the attached state is determined to be good.

To inform the user for the poor attachment, the processing unit 17 further controls a display device 11 to show an indication signal when the attached state is determined to be bad, or controls other means to indicate corresponding signals.

The light source 1533 is only used in the attachment confirming phase or is also used in the physiological characteristic detecting phase. In one non-limiting embodiment, the physiological detection device 15 further includes other light sources 1531 arranged at other two sides of the sensor array 151 for detecting the physiological characteristics. The light sources 1531 preferably emit red light or infrared light.

Figure 7:
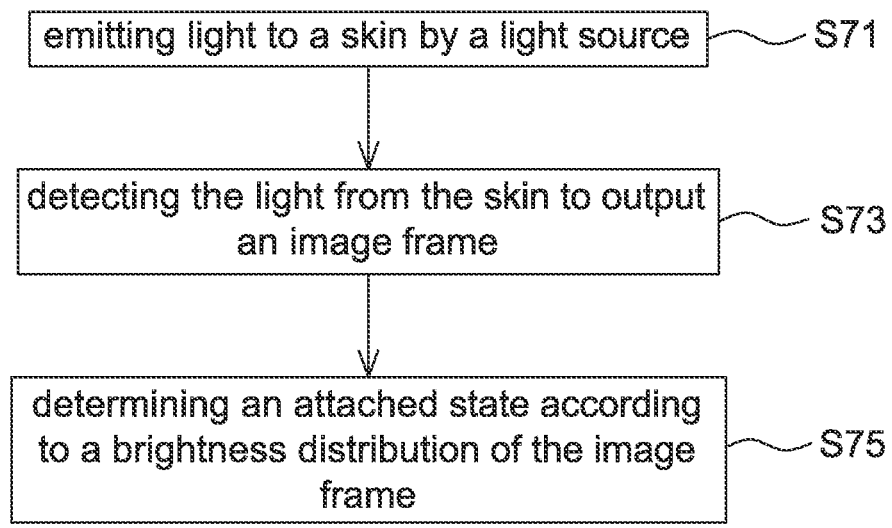
FIG. 7 is a flow chart of an operating method of a physiological detection device according to the second embodiment of the present disclosure.

Referring to FIG. 7, it is a flow chart of an operating method of a physiological detection device according to the second embodiment of the present disclosure. The operating method includes the steps of: emitting light to a skin by a light source (Step S71); detecting the light from the skin to output an image frame (Step S73); and determining an attached state according to a brightness distribution of the image frame (Step S75). The brightness distribution includes a covering range, a center and/or a size of bright pixels. Details of the operating method have been illustrated above and thus are not repeated herein.

Figure 8:
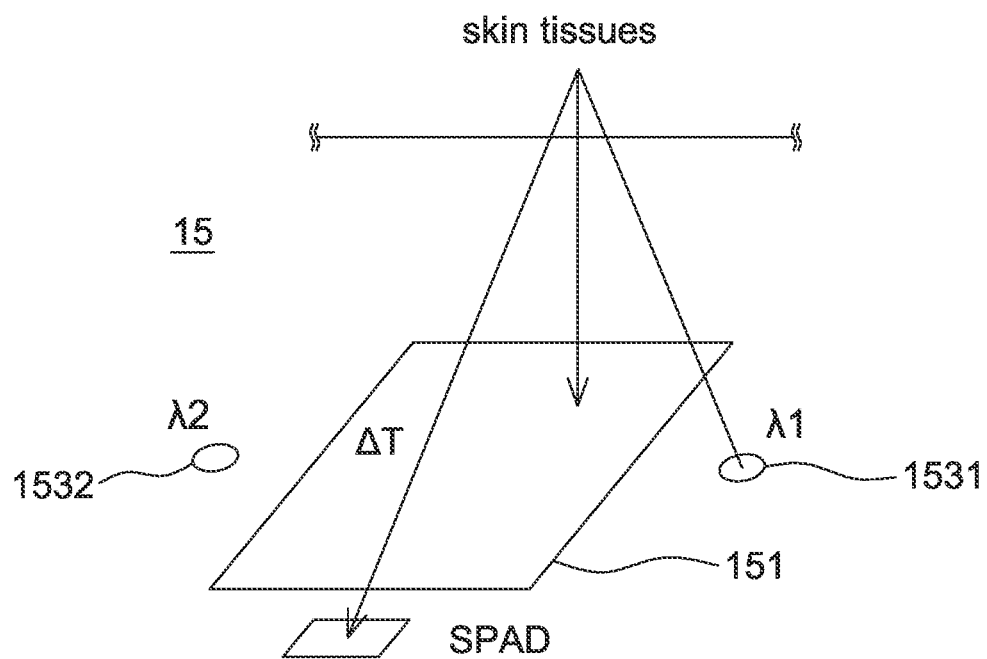
FIG. 8 is a schematic diagram of a physiological detection device according to a third embodiment of the present disclosure.

Referring to FIG. 8, it is a schematic diagram of a physiological detection device according to a third embodiment of the present disclosure. The physiological detection device 15 includes a first light source 1531, a SPAD and a processing unit 17.

The first light source 1531 emits light of a first wavelength $2d$ to illuminate a skin, and the first wavelength $2d$ is preferably selected from one wavelength between green light spectrum and infrared light spectrum.

The single photon avalanche diode (SPAD) receives light from the skin to output an electrical pulse signal. The processing unit 17 is electrically connected to the first light source 1531 and the SPAD, and calculates a first time-of-flight according to the electrical pulse signal from the SPAD and determines an attached state by comparing the first time-of-flight with a first time threshold. More specifically, the processing unit 17 controls the first light source 1531 to emit light and starts to count a passed time before the SPAD receives the reflected or scattered light from the skin. This time-of-flight of the light from the first light source 1531 to the SPAD is used as a reference to identify the distance between the physiological detection device 15 and the skin.

One method of calculating a time-of-flight is referred to U.S. application Ser. No. 16/129,804, filed on Sep. 13, 2018 and assigned to the same assignee of the present application, and the full disclosure of which is incorporated herein by reference.

In the third embodiment, the processing unit 17 determines an attached state being good when the time-of-flight is smaller than the time threshold (i.e. distance smaller than a predetermined distance threshold); and determines the attached state being bad when the time-of-flight is larger than the time threshold (i.e. distance larger than the predetermined distance threshold).

To increase the confirmation accuracy, the physiological detection device 15 further includes a second light source 1532 used to emit light of a second wavelength $\lambda 2$ to illuminate the skin. Since light of different wavelengths penetrates different depths in skin tissues, the reflected or scattered light reaches the SPAD at different time points. Accordingly, the processing unit 17 calculates a second time-of-flight according to the electrical pulse signal from the SPAD corresponding to lighting of the second light source 1532 and determines the attached state by further comparing the second time-of-flight with a second time threshold. Calculating multiple time-of-flights is for double checking. Similarly, a wavelength difference between the first and second wavelengths is preferably more than 50 nm. The first and second time thresholds are previously determined and stored in the memory 19.

Similarly, the processing unit 17 further controls a display device 11 to show an indication signal when the first time-of-flight is larger than the first time threshold, or controls other means to indicate corresponding signals.

The SPAD in the third embodiment is for confirming the attached state but not for detecting the physiological characteristics. The physiological detection device 15 further includes a CMOS sensor array 151 electrically connected to the processing unit 17 for performing the physiological detection. The first light source 1531 and/or the second light source 1532 are also used in the physiological detection. The SPAD is arranged inside or outside the CMOS sensor array 151 without particular limitations. In other aspects, the CMOS sensor array 151 is replaced by a SPAD array.

To reduce the power consumption of the physiological detection device 15, preferably the processing unit 17 further turns off the CMOS sensor array 151 when the first time-of-flight is larger than the first time threshold. More specifically, the CMOS sensor array 151 is turned on only when the attached state or wearing state is confirmed to be good.

Figure 9:
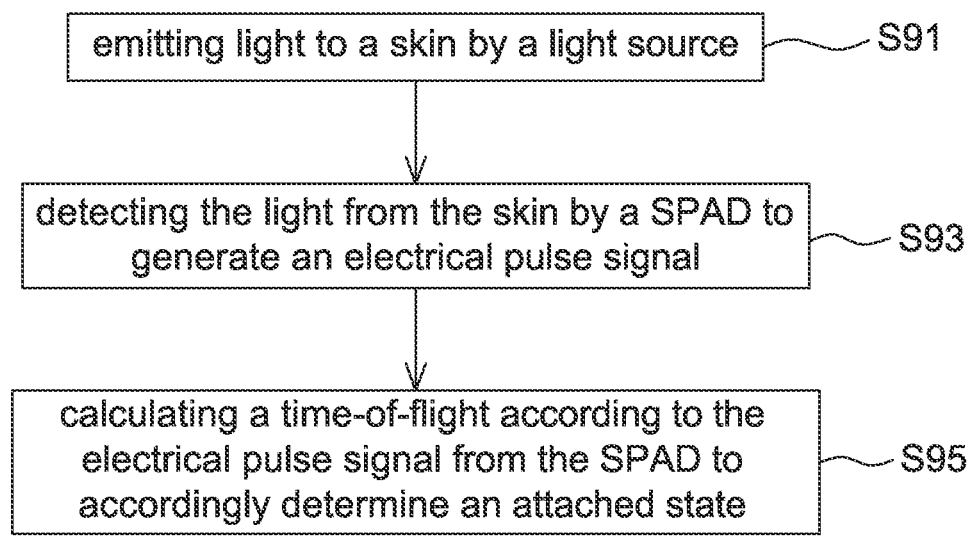
FIG. 9 is a flow chart of an operating method of a physiological detection device according to the third embodiment of the present disclosure.

Referring to FIG. 9, it is a flow chart of an operating method of a physiological detection device according to the third embodiment of the present disclosure. The operating method includes the steps of: emitting light to a skin by a light source (Step S91); detecting the light from the skin by a SPAD to generate an electrical pulse signal (Step S93); and calculating a time-of-flight according to the electrical pulse signal from the SPAD to accordingly determine an attached state (Step S95). Details of this operating method have been illustrated above, and thus details thereof are not repeated herein.

In some other aspects, some structures and methods of the above first to third embodiments are implemented together for double checking the attached state or the wearing state.

It should be mentioned that the size and the spatial relationship of elements in the drawings of the present disclosure are only intended to illustrate but not to limit the present disclosure.

Furthermore, the method of detecting the physiological characteristic using a sensor array and a light source is known to the art, and thus details of the physiological detection are not described herein. Although some embodiments of the present disclosure use the sensor array to output image frames in the attachment confirming phase, the processing unit processes the image frames in different ways from calculating the physiological characteristic in the physiological characteristic detecting phase. In the present disclosure, the light source used in the attachment confirming phase may or may not be used in the physiological characteristic detecting phase according to different applications.

In the present disclosure, after the attached state or wearing state is confirmed using the above embodiments, the physiological detection device 15 generates the PPG signal according to the pixel data from the sensor array 151 and calculates the physiological characteristics according to the PPG signal using the conventional ways. The present disclosure is to confirm whether the attached state is suitable to detect correct physiological characteristics. That is, the operating methods shown in FIGS. 4, 7 and 9 are for the attachment confirming phase. Once the attached state or wearing state is confirmed to be good, based on comparing detected signals with a predetermined threshold, these operating methods are not performed during detecting the physiological characteristics. In some other aspects, these operating methods are performed at a lower frequency during detecting the physiological characteristics to confirm the attached state or wearing state, e.g., entering the attachment confirming phase from time to time automatically or manually, e.g., by pressing or pulling the knob 13 by a user.

As mentioned above, it is crucial to determine at first whether a physiological detection device is well attached to a skin surface to obtain accurate physiological characteristics. Accordingly, the present disclosure further provides a physiological detection device (e.g., FIGS. 2, 5 and 8) and operating method thereof (e.g., FIGS. 4, 7 and 9) that confirm an attached state or wearing state using the optical detecting means and control a display device or other indication means to show the calculated physiological characteristics and an indication signal for informing the user to adjust the attachment of the physiological detection device on his/her body.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A physiological detection device, comprising:
   a polarizing layer, comprising a first region and a second region having different polarization directions;
   a sensor array, opposite to the polarizing layer and configured to receive light from a skin to output pixel data; and
   a processing unit, electrically connected to the sensor array to receive the pixel data, and configured to
      generate a first detected signal associated with the first region,
      generate a second detected signal associated with the second region, and
      compare the first detected signal with the second detected signal to determine an attached state of the physiological detection device with respect to the skin.

2. The physiological detection device as claimed in claim 1, wherein the sensor array is a photodiode array or a single photon avalanche diode array.

3. The physiological detection device as claimed in claim 1, wherein
   the sensor array is configured to successively receive light of a first wavelength and a second wavelength, which is different from the first wavelength, from the skin, and
   the first detected signal and the second detected signal are generated associated with the light of the first wavelength.

4. The physiological detection device as claimed in claim 3, wherein the processing unit is further configured to
   generate a third detected signal associated with the first region and the light of the second wavelength,
   generate a fourth detected signal associated with the second region and the light of the second wavelength, and
   compare the first and second detected signals respectively with the third and fourth detected signals to determine the attached state.

5. The physiological detection device as claimed in claim 3, wherein a wavelength difference between the first and second wavelengths is at least 50 nm.

6. The physiological detection device as claimed in claim 1, wherein the first and second detected signals are average brightness values or amplitudes of a photoplethysmography signal respectively associated with the first region and the second region.

7. The physiological detection device as claimed in claim 6, wherein the processing unit is configured to
   determine the attached state being good when a difference between the first detected signal and the second detected signal is lower than a difference threshold, and
   determine the attached state being bad when the difference between the first detected signal and the second detected signal is larger than the difference threshold.

8. The physiological detection device as claimed in claim 7, wherein the processing unit is further configured to control a display device to show an indication signal when the attached state is determined to be bad.

9. The physiological detection device as claimed in claim 1, wherein the polarizing layer further comprising a third region and a fourth region having different polarization directions from those of the first region and the second region.

10. The physiological detection device as claimed in claim 3, wherein
 the first wavelength is a wavelength of green light, and
 the second wavelength is a wavelength of infrared light.

* * * * *